United States Patent [19]

Holland et al.

[11] Patent Number: 4,650,883
[45] Date of Patent: Mar. 17, 1987

[54] HEXAHYDRO-3-FLUORO-4-OCTENYL-2H-CYCLOPENTA[β]FURAN-2-ONES

[75] Inventors: George W. Holland; Perry Rosen, both of North Caldwell, N.J.; Hans Maag, Münchenstein, Switzerland

[73] Assignee: Hoffmann-La Roche Inc., Nutley, N.J.

[21] Appl. No.: 773,914

[22] Filed: Sep. 9, 1985

Related U.S. Application Data

[60] Division of Ser. No. 414,765, Sep. 7, 1982, Pat. No. 4,558,142, which is a continuation-in-part of Ser. No. 337,791, Jan. 7, 1982, abandoned, which is a continuation-in-part of Ser. No. 242,818, Mar. 11, 1981, abandoned.

[51] Int. Cl.$^4$ .......................................... C07D 307/93
[52] U.S. Cl. ..................................................... 549/312
[58] Field of Search .......................................... 549/312

[56] References Cited

U.S. PATENT DOCUMENTS

| | | |
|---|---|---|
| 4,031,081 | 6/1977 | Magerlein .......................... 549/312 |
| 4,456,768 | 6/1984 | Fried .................................... 560/53 |
| 4,472,428 | 9/1984 | Toru et al. ........................ 549/214 |

FOREIGN PATENT DOCUMENTS

| | | |
|---|---|---|
| 0054795 | 6/1982 | European Pat. Off. . |
| 0172543 | 12/1980 | Japan . |
| 2088856 | 6/1982 | United Kingdom . |

Primary Examiner—Jane T. Fan
Attorney, Agent, or Firm—Jon S. Saxe; George M. Gould; William H. Epstein

[57] ABSTRACT

The prostacyclins 7-fluoro-6,9-epoxy-16-substituted-15-hydroxyprost-[4 or 5,13]-dienoic acids and esters useful as anti-secretory agents, blood pressure lowering agents, anti-ulcerogenic agents, anti-hypertensive agents, bronchodilation agents and for combating gastro-hyperacidity and as anti-blood platelet aggregating agents.

4 Claims, No Drawings

HEXAHYDRO-3-FLUORO-4-OCTENYL-2H-CYCLOPENTA[β]FURAN-2-ONES

CROSS REFERENCE TO RELATION APPLICATION

This application is a divisional of Ser. No. 414,765, filed Sept. 7, 1982, now U.S. Pat. No. 4,558,142 issued on Dec. 10, 1985; which in turn is a continuation-in-part of Ser. No. 337,791, filed Jan. 7, 1982 now abandoned, which in turn is a continuation-in-part application of Ser. No. 242,818 filed Mar. 11, 1981, Holland, Maag and Rosen, now abandoned.

SUMMARY OF THE INVENTION

In accordance with this invention, compounds of the formula

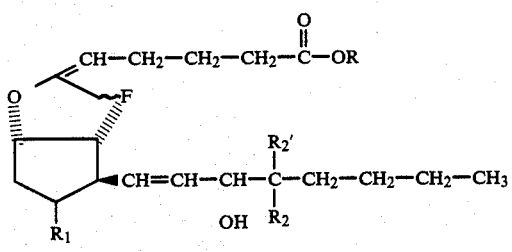

and

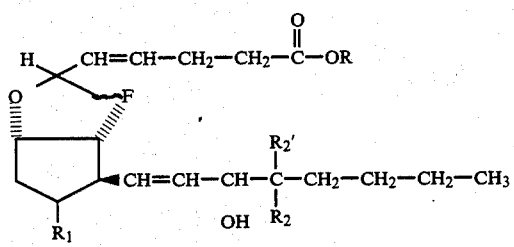

wherein R is hydrogen or lower alkyl; $R_1$ is hydrogen, hydroxy or methyl; or $R_2$ is hydrogen, methyl or fluoro; and $R_2'$ is fluoro, hydrogen, trifluoromethyl or methyl; and with the proviso that when $R_2'$ is trifluoromethyl, $R_2$ is hydrogen or methyl
and salts thereof as well as optical antipodes and racemates thereof are useful as anti-secretory agents, anti-hypertensives, anti-ulcerogenic agents, blood pressure lowering agents and for combating gastro-hyperacidity and for anti-blood platelet aggregating agents.

The compounds of formulas I-A and I-B are prepared from compounds of the formula:

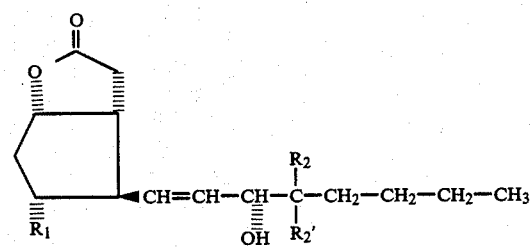

wherein $R_1$, $R_2$ and $R_2'$ are as above
or optical antipodes or racemates thereof.

DETAILED DESCRIPTION OF THE INVENTION

As used throughout this application, the term "lower alkyl" includes both straight chain and branched chain alkyl groups having from 1 to 7 carbon atoms such as methyl and ethyl. As also used herein, the term "lower alkanoic acids" comprehends an alkanoic acid of 1 to 7 carbon atoms such as formic acid and acetic acid. As further used herein, the term "halogen" or "halo", unless otherwise stated, comprehends fluorine, chlorine, bromine and iodine. Alkali metal includes all alkali metals such as lithium, sodium and potassium.

In the process of this invention, all compounds having one or more asymmetric carbon atoms can be produced as racemic mixtures. These racemic mixtures which are obtained can be resolved at the appropriate steps in the process of this invention by methods well known in the art whereupon subsequent products may be obtained as the corresponding optically pure enantiomers. On the other hand, the claimed optically active enantiomer or racemates of formula I can be produced depending upon the optical form of the compound of formula II utilized as a starting material.

In the pictorial representation of the compounds given throughout this application, a thickened taper line (▼) indicates a substituent which is in the beta-orientation (above the plane of the molecule), a dotted line (ıııı) indicates a substituent which is in the alpha-orientation (below the plane of the molecule) and in a wavy line (∼) indicates a substituent which is in either the alpha- or beta-orientation or mixtures of these isomers. It is to be understood that the pictorial representations of the compounds given throughout the specification are set forth for convenience and are to be construed as inclusive of other forms including enantiomers and racemates and are not to be construed as limited to the particular form shown.

The compounds of formulas I-A and I-B as well as their optical antipodes and racemates are active as antisecretory agents, bronchodilators, anti-blood platelet aggregators, anti-ulcerogenic agents, anti-hypertensive agents and blood pressure lowering agents.

As also used herein, the term "aryl" signifies mononuclear aromatic hydrocarbon groups such as phenyl, tolyl, etc. which can be unsubstituted or substituted in one or more positions with a lower alkylenedioxy, nitro, halo, a lower alkyl or a lower alkoxy substituent, and polynuclear aryl groups such as naphthyl, anthryl, phenanthryl, azulyl, , etc., which can be unsubstituted or substituted with one or more of the aforementioned groups. The preferred aryl groups are the substituted and unsubstituted mononuclear aryl groups, particularly phenyl.

The term "ether protecting group removable by acid catalyzed cleavage" designates any ether which, upon acid catalyzed cleavage yields the hydroxy group. A suitable ether protecting group is, for example, the tetrahydropyranyl ether, or 4-methyl-5,6-dihydro-2H-pyranyl ether. Others are arylmethyl ethers such as benzyl, benzylhydryl, or trityl ethers or alpha-lower alkoxy lower alkyl ether, for example, methoxymethyl or allylic ethers, or tri(lower alkyl)silyl ethers such as trimethyl silyl ether or dimethyl-tert-butyl silyl ethers. The preferred ethers which are removed by acid catalyzed cleavage are t-butyl and tetrahydropyranyl and the tri(lower alkyl)silyl ethers, particularly dimethyl-tert-butyl ethers. Acid catalyzed cleavage is carried out by treatment with a strong organic or inorganic acid. Among the preferred inorganic acids are the mineral acids such as sulfuric acid, hydrohalic acid, etc. Among the preferred organic acids are lower alkanoic acids such as acetic acid, para-toluene sulfonic acid, etc. The acid catalyzed cleavage can be carried out in an aqueous medium or in an organic solvent medium. Where an organic acid is utilized, the organic acid can be the solvent medium. In the case of t-butyl, an organic acid is generally utilized with the acid forming the solvent medium. In the case of tetrahydropyranyl ethers, the cleavage is generally carried out in an aqueous medium. In carrying out this reaction, temperature and pressure are not critical and this reaction can be carried out at room temperature and atmospheric pressure.

That the prostacyclins of formulas I-A and I-B of this invention are active as anti-blood platelet aggregating agents can be seen from the administration of $(5Z,7\beta,9\alpha,11\alpha,13E,15R)$-7-fluoro-6,9-epoxy-11,15-dihydroxy-16,16-dimethyl-prosta-5,13-dien-1-oic acid methyl ester by the following test.

30 Ml. of blood was drawn from the jugular vein of a conscious beagle using two 15 ml. Vacutainer tubes, with no additive, connected to a 20 g. 1 inch multiple sample needle. The blood was immediately transferred to a 50 ml. conical plastic centrifuge tube containing 3 ml. of 3.8% sodium citrate (3.8 grams of sodium citrate crystal, $Na_3C_6H_5O_7.2H_2O$, in 100 ml. of distilled water), capped and gently mixed. The citrated blood was centrifuged at 160 g. for 15 minutes at 20° C. The platelet rich plasma (PRP) was carefully withdrawn with a pipette, without disturbing the buffy coat and erythrocyte layers. The PRP was placed in 16×125 mm plastic tubes, capped and stored at room temperature 19°-21° C. PRP preparations showing a tinge of redness, indicative of hemolysis, were discarded. The remaining blood, after the removal of PRP, was recentrifuged at higher speed, 900 g. for 10 minutes, to yield platelet poor plasma (PPP). The PRP was used immediately and the aggregation study completed within three hours after preparation.

Platelet aggregation was measured with a Payton duel channel aggregation module connected to a duel pen recorder for the continuous recording of the increase in light transmission due to clumping of platelets. The 0–100% transmission scale was set with PRP (0%) and PPP (100%). The temperature was set at 37° and the stirring speed at 900 rpm. 0.45 Ml. of PRP was added to a cuvette containing a teflon coated stirring bar and prewarmed at 37° in a water bath. 5 µl of various concentrations of $(5Z,7\beta,9\alpha,11\alpha,13E,15R)$-7-fluoro-6,9-epoxy-11,15-dihydroxy-16,16-dimethyl-prosta-5,13-dien-1-oic acid methyl ester, diluted from a stock solution of $5 \times 10^{-4}$M in DMSO (dimethylsulfoxide) with phosphate buffered saline containing 1 mg/ml. of bovine serum albumin, fraction V, was added and stirred for 1 minute. The inducer of aggregation, arachidonic acid, at a concentration which will cause 50–70% aggregation after 5 minutes, was then added in 50 µl of solution. The % inhibition, set forth in the following Table, was calculated from the ratio of the % aggregation with $(5Z,7\beta,9\alpha,11\alpha,13E,15R)$-7-fluoro-6,9-epoxy-11,15-dihydroxy-16,16-dimethyl-prosta-5,13-dien-1-oic acid methyl ester over that with the vehicle×100.

| Concentration of $(5Z,7\beta,9\alpha,11\alpha,13E,15R)$-7-fluoro-6,9-epoxy-11,15-dihydroxy-16,16-dimethyl-prosta-5,13-dien-1-oic acid methyl ester | % Inhibition |
| --- | --- |
| $1 \times 10^{-13}$ M | 14.2 |
| $3 \times 10^{-13}$ M | 20.8 |
| $1 \times 10^{-12}$ M | 71.4 |
| $1 \times 10^{-11}$ M | 57.8 |
| $1 \times 10^{-10}$ M | 20.8 |

The preparation of phosphate buffered saline and arachidonic acid solution used above is as follows: Phosphate buffered saline (PBS) was prepared by adding 1 mM solution of sodium phosphate aqueous buffer, pH 7.4 to 0.85% by weight/volume of an aqueous sodium chloride solution. Arachidonic acid solution was prepared as follows: A stock solution of 10 mg. per ml. in absolute ETOH was prepared and stored in freezer. To make a 10 mM solution, 0.3 ml. of the stock solution was evaporated to near dryness under nitrogen and redissolved in 0.75 ml. of $0.02NH_4OH$ (freshly prepared) and 0.2 ml. of PBS. Further dilutions of arachidonic acid were made with $NH_4OH$ and PBS mixture.

The compounds of formulae I-A and I-B or their pharmaceutically acceptable salts can be used in a variety of pharmaceutical preparations. In these preparations, the new compounds are administerable in the form of tablets, pills, powders, capsules, injectables, solutions, suppositories, emulsions, dispersions, and in other suitable forms. The pharmaceutical preparations which contain the compounds of formulae I-A and I-B are conveniently formed by admixing with a non-toxic pharmaceutical organic carrier or a non-toxic pharmaceutical inorganic carrier. Typical of pharmaceutically acceptable carriers are, for example, water, gelatin, lactose, starches, magnesium stearate, talc, vegetable oils, polyalkylene glycols, petroleum jelly and other conventionally employed pharmaceutically acceptable carriers. The pharmaceutical preparations may also contain non-toxic auxiliary substances such as emulsifying, preserving and wetting agents and the like, as for example, sorbitan monolaurate, triethanol amine oleate, polyoxyethylene sorbitan, dioctyl sodium sulfosuccinate and the like.

The daily dose administered for the compounds will, of course, vary with the particular novel compound employed because of the very potency of the compounds, the chosen route of administration and the size of the recipient. The dosage administered is not subject to definite bounds but it will usually be in effective amounts of the pharmacologically function of the prostacyclin. Representative of a typical method for administering the prostacyclin compounds of formulae I-A and I-B is by oral administration. By this route, the prostacyclins of formulae I-A and I-B can be administered at a dosage of 0.1 micrograms to 0.30 micrograms per day per kilogram of body weight.

Among the preferred compounds of formulae I-A and I-B are those compounds where the 7-fluoro substituent is in the beta configuration. Among the 7-beta fluoro compounds, the following are preferred:

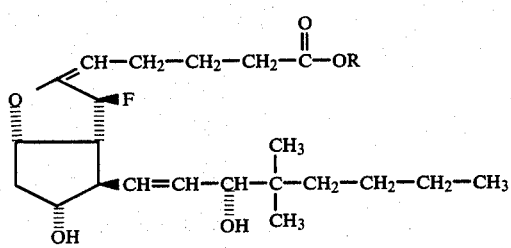
I-Ai
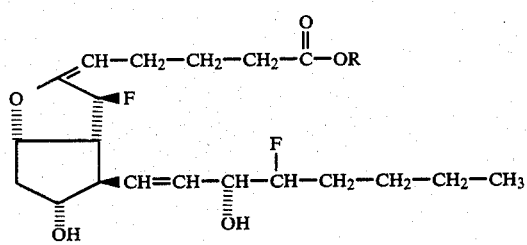
I-Aii
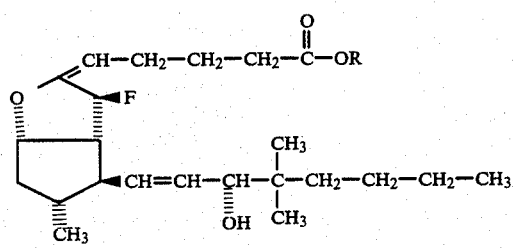
I-Aiii
and
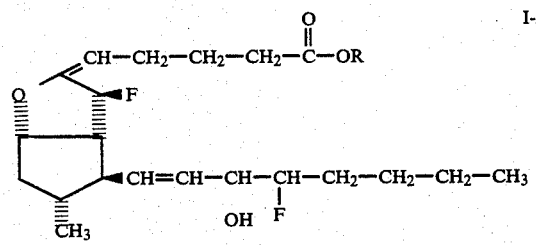
I-Aiiii
When R is lower alkyl in the compound of formulae I-Ai, I-Aii, I-Aiii and I-Aiiii, R is preferably methyl or ethyl.
The compounds of formulae I-A and I-B are prepared by the compound of formula II via the following intermediates:
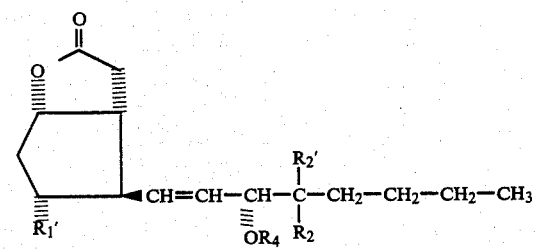
IV
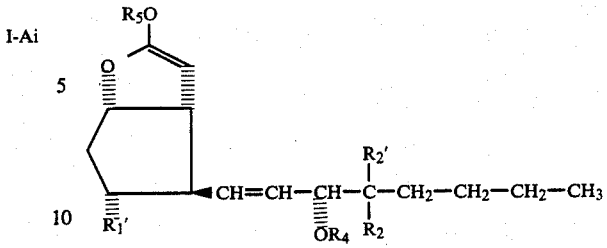
V
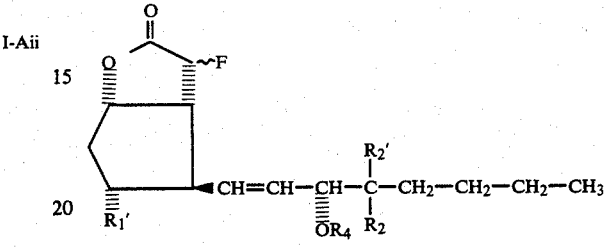
VI
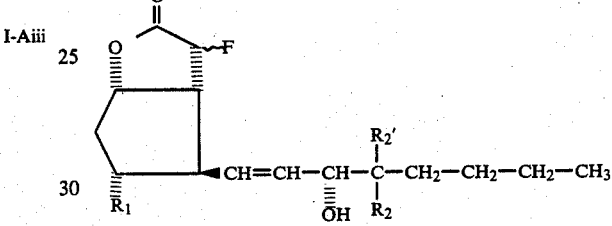
VII
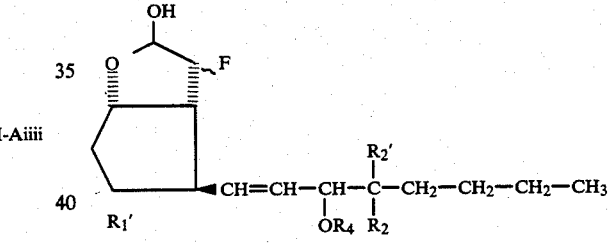
VIII
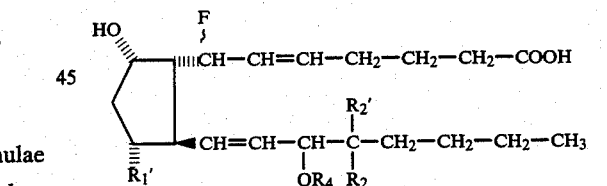
IX
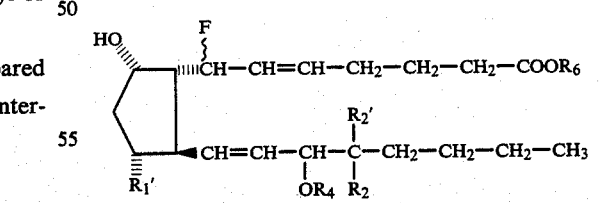
X
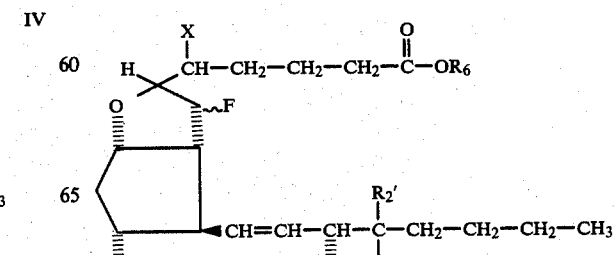
XI

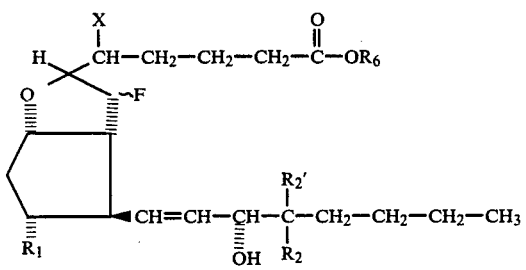

XII

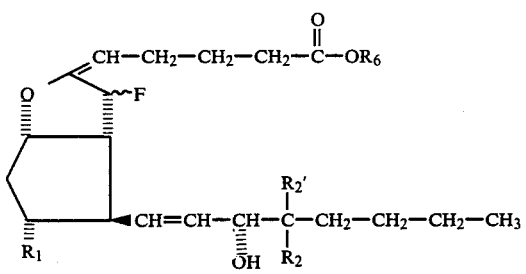

XIII

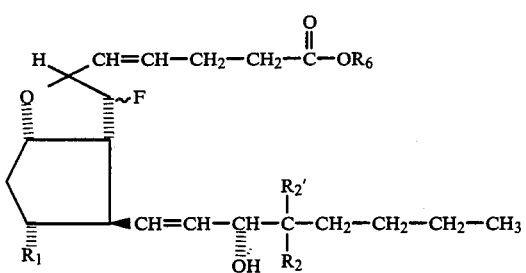

XIV

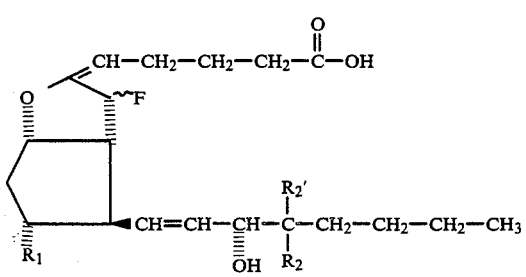

XV

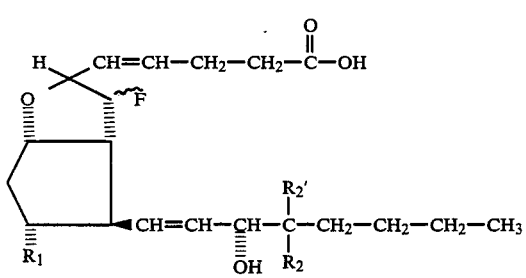

XVI wherein R, $R_1$, $R_2$ and $R_2'$ are as above, $R_1'$ is hydrogen, methyl or $OR_4$; —$OR_4$ form an ether protecting group removable by an acid catalyzed cleavage; $R_6$ is lower alkyl and X is halogen; and $R_5$ is tri(lower alkyl)silyl.

The compound of formula II is converted to the compound of formula IV by conventional etherification in order to protect any free hydroxy groups in the compound of formula II. Where $R_1$ is hydroxy in the compound of formula II, this etherification converts the hydroxy group to the protected ether in the compound of formula IV. The preferred ethers for use in this reaction are tetrahydropyranyl and dimethyl-t-butyl silyl ether. In carrying out this reaction, any conventional method of etherifying the compound of formula II can be utilized in forming the compound of formula IV. When a tri(lower alkyl)silyl ether is desired, a tri(lower alkyl)chlorosilane is utilized as the etherifying agent in the presence of an organic base such as imidazol or pyridine. Any conventional organic amine base can be utilized in carrying out this reaction.

The compound of formula IV is converted to the compound of formula V by first enolizing the compound of formula IV and then treating the compound of formula IV with a tialkyl halosilane. Enolization is accomplished by enolizing the compound of formula IV. Any conventional method of enolizing can be utilized to carry out this reaction. Among the preferred methods is by treating the compound of formula IV with a non-aqueous alkali metal base. The preferred base for use in this reaction is lithium diisopropyl amide or sodium hexamethyldisilazane. In carrying out the reaction utilizing the non-aqueous alkali metal base, temperatures of $-70°$ to $-30°$ are generally preferred. Generally, this reaction is carried out in an inert organic solvent. Any conventional inert organic solvent which is a liquid at the aforementioned temperatures can be utilized. Among the preferred solvents are tetrahydrofuran. The enolate of the compound of formula IV in the form of its alkali metal salt is converted to the compound of formula V by treating the compound of formula V with a trialkyl halosilane, preferably trimethylchlorosilane. Generally, this reaction is carried out at the same temperatures as in the same solvent utilized to form the enolate.

The compound of formula V is converted to the compound of formula VI by treating the compound of formula V with a fluorinating agent. Any conventional fluorinating agent can be utilized in carrying out this reaction. Among the preferred fluorinating agents are xenon difluoride, fluorine gas, etc. Generally, this reaction is carried out in the presence of an inert organic solvent. Any conventional inert organic solvent can be utilized in carrying out this reaction. Among the preferred solvents are halogenated hydrocarbons such as methylene chloride, carbon tetrachloride, etc. In carrying out his reaction, temperature and pressure are not criitical and this reaction can be carried out at room temperature and atmospheric pressure. While room temperature can be utilized, it is preferred to carry out this reaction at low temperatures, i.e. from $-10°$ C. to $+10°$ C.

In converting the compound of formula V to the compound of formula VI, the compound of formula V is produced as a mixture of the following compounds:

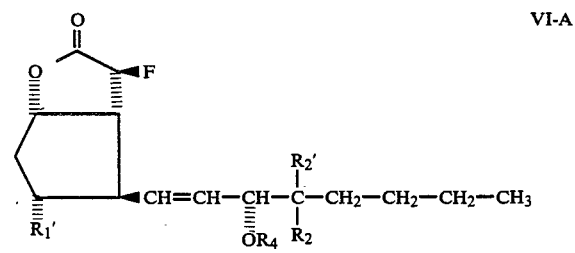

VI-A and

-continued

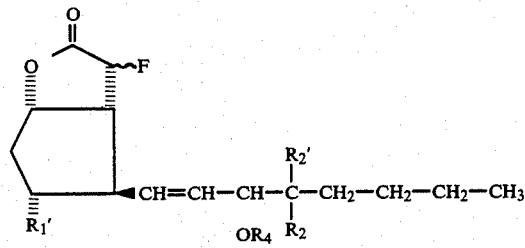
VI-B wherein $R_1'$, $R_2$ and $R_2'$ are as above.

The compounds of formulae VI-A and VI-B can be separated by conventional methods such as chromatography. On the other hand, the compounds of formula VI as a mixture of the compounds of formulae VI-A and VI-B can be utilized throughout the rest of the reaction or, if desired, separated at some later state in the reaction scheme to produce the compound of formulae I-A or I-B having the desired fluoro orientation at the 7-position. If the compound of formula VI is separated into the compound of formulae VI-A and VI-B, the same configuration of the fluorine atom is carried out throughout the rest of the reaction. Therefore, if the compounds of formulae I-A or I-B wherein the fluorine atom is at the 7-beta position, the compound of formula VI-A is utilized in the rest of the reaction scheme producing compounds of the formulae VII through XVI wherein the fluorine atom set forth in these formulae is in the beta position. If the compounds of I-A and I-B are desired wherein the fluorine is in the 7-alpha position, then the compound of formula VI-B is utilized in the reaction scheme to produce the compounds of formulae VI through XVI wherein the fluorine atom shown in these formulae is in the alpha position.

On the other hand, the compound of formula VI can be utilized without separating it into the compounds of formulae VI-A and VI-B. In this manner, the compounds of formulae I-A and I-B wherein the fluorine is in both of the alpha and beta positions is produced via intermediates of the formulae VII through XVI having the fluoro group in the same position as shown.

In converting the compound of formula II to the compound of formula VI, it is generally preferred to utilize the tri(lower alkyl)silyl ethers as the hydroxy protecting group. In the conversion of the compounds of formula VI to the compounds of formulae I-A and I-B, it is generally preferred to protect one or more of the hydroxy groups with a tetrahydropyranyl ether. On the other hand, the silyl ethers or any other conventional ethers can be utilized in the rest of this process. However, in accordance with the preferred embodiment, the silyl ethers of formula VI are hydrolyzed to produce the compound of formula VII which is then reetherified to produce the compound of formula VI within the ether group is tetrahydropyranyl. Any conventional method of hydrolyzing ethers can be utilized to carry out the conversion of the compounds of formula VI to the compounds of formula VII and any conventional method of etherification can be utilized to carry out the reconversion of the compounds of formula VII to the compounds of formula VI. With tetrahydropyranyl as the protecting group in the compound of formula VI, there is no need to hydrolyze the compound of formula VI to the compound of formula VII since the compound of formula VII can be produced directly from the compound of formula VI.

The compound of formula VII is converted to the compound of formula VIII by treating the compound of formula VII with a reducing agent. In carrying out this reaction, any conventional reducing agent which will selectively reduce a keto-group to a hydroxy-group can be utilized. Preferred reducing agents are the hydrides, particularly the aluminum hydrides such as alkali metal aluminum hydride, and the borohydrides such as alkali metal borohydrides, with diisobutyl aluminum hydride being particularly preferred. Also, this reaction can be carried out utilizing di-branched chain lower alkyl)boranes such as bis(3-methyl-2-butyl)borane. In carrying out this reaction, temperature and pressure are not critical and the reaction can be carried out at room temperature and atmospheric pressure or at elevated or reduced temperatures and pressures. Generally, it is preferred to carry out this reaction at a temperature of from $-80°$ C. to the reflux temperatue of the reaction mixture. This reduction reaction can be carried out in the presence of an inert organic solvent. Any conventional inert organic solvents can be utilized in carrying out his reaction. Among the preferred solvents are dimethoxy ethylene glycol, and the ethers such as tetrahydrofuran, diethyl ether and dioxane.

The compound of formula IX is obtained from the compound of formula VIII by reacting the compound of formula VIII with phosphonium salts of the formula:

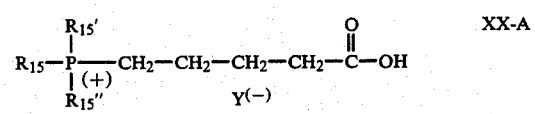

wherein $R_{15}$, $R_{15}'$, $R_{15}'$ is aryl or di(lower alkyl)-amino; and Y is halogen via a conventional Wittig type reaction. Any of the conventional conditions in Wittig reactions can be utilized in carrying out this reaction.

The compound of formula IX can be converted to a compound of the formula X by esterification with diazomethane or a reactive derivative of a lower alkanol such as a lower alkyl halide. Any conventional conditions utilizing in these esterifying reactions can be utilized to form the compound of formula X from the compound of formula IX.

The compound of formula X is converted to the compound of formula XI by treating the compound of formula X with a halogenating agent. Among the preferred halogenating agents are included N-halosuccinimides, particularly N-iodosuccinimide. Generally, this reaction is carried out in the presence of a polar solvent such as acetonitrile and halogenated hydrocarbons such as methylene chloride, ethylene chloride, etc. In fact, any conventional polar organic solvent can be utilized. In carrying out this reaction, temperatures of from 0° to 35° C. can be utilized. Generally, it is preferred to carry out this reaction at room temperature.

The compound of formula XI is converted to the compound of formula XII by ether hydrolysis. Any conventional method of ether hydrolysis can be utilized to carry out this reaction. Generally, it is preferred to utilize mild acid hydrolysis such as aqueous acetic acid.

In the next step, the compound of formula XII is treated with a dehydrohalogenating agent to produce the compounds of formulae XIII and XIV in admixture. In carrying out this reaction, any conventional dehydrohalogenating agent can be utilized. Among the preferred dehydrohalogenating agents are the diazabicycloalkanes or alkknes such as 1,8-diazabicyclo[5.4.0]undec-7-ene and 1,4-diazabicyclo[2.2.2]octane. Furthermore, any other conventional organic base utilized for dehydrohalogenation can be utilized in carrying out this reaction. This reaction produces the compounds of formula XIII and the compounds of formula XIV in admixture. The compounds of formula XIII can be separated from the compounds of formula XIV by any conventional procedure such as chromatography.

The compound of formula XIII is converted to the compound of formula XV and the compound of formula XIV is converted to the compound of formula XVI by hydrolysis. Any conventional method of ester hydrolysis can be utilized in carrying out these reactions. Among the preferred method of ester hydrolysis is either treating the compound of formula XIII or the compound of formula XIV with a alkali metal hydroxide. Among hhe preferred alkali metal hydroxides for use in this reaction are sodium and potassium hydroxides.

In the practice of this invention, any pharmaceutically acceptable basic salts of the compound of formula I-A and I-B where R is hydrogen can be utilized. Among the preferred pharmaceutically acceptable basic salts are included the alkali metal salts such as lithium, sodium, and potassium, with sodium being especially preferred. Other salts which are also preferred are the alkaline earth metal salts such as calcium and magnesium, amine salts such as the lower alkyl amines, e.g. ethylamine and the hydroxy-substituted lower alkyl amine salts and tris(hydroxymethyl)aminomethane. Also preferred are the ammonium salts. Among the other salts are dibenzylamine, monoalkylamines or dialkylamine and salts with amino acids (i.e. salts with arginine and glycine).

Among the preferred compounds of this invention are compounds of the formula XIII and XV where $R_1$ and $R_2$ are both hydrogen.

The following examples are illustrative but not limitative of the invention. In the examples, the ether utilized was diethyl ether. All temperatures are in degrees Centigrade. The petroleum ether utilized in the examples had a boiling point of from 35° to 60° C. In the examples, "h" indicates hours.

EXAMPLE 1

[3aR-[3aα,4α(1E,3R*),5β,6aα]]-Hexahydro-5-[[(1,1-dimethylethyl)dimethylsilyl]oxy]-4-[[[3-(1,1-dimethylethyl)dimethylsilyl]oxy]-4,4-dimethyl-l-octenyl]-2H-cyclopenta[b]furan-2-one 502.2 mg (1.69 mmol) of [3aR-[3aα,4α(IE,3R*),5β,6aα]]-hexahydro-5-hydroxy-4-(3-hydroxy-4,4-dimethyl-l-octenyl)-2H-cyclopenta[b]furan-2-one, was dissolved in 15 mL of dimethylformamide (reagent grade, dried over 3A molecular sieves) under a positive argon pressure. 1.045 g (6.93 mmol=4.09 eq.) of t-butyldimethylchlorosilane (dist. before use) and 587.6 mg (8.63 mmol=5.09 eq.) of imidazole (reagent grade) were added. The resulting mixture was stirred at room temperature for 18 h, poured into 60 ml ice cold 0.5N aqueous HCl and extracted three times with 60 ml of diethylether. The extracts were washed with 60 ml of a mixture of sat. aqueous $NaHCO_3/H_2O$/brine=1:1:2 followed by washing with 60 ml brine. The extracts were combined, dried over $MgSO_4$ and concentrated at reduced pressure. 1.25 g of a white semi-solid remained.

The crude product was chromatographed on a 75 g silica gel column with 10% by volume ether/90% by volume petroleum ether (first 1 lt) followed by 20% by volume ether/80% by volume petroleum ether. 857.1 mg (1.63 mmol, 96.4%) of [3aR-[3aα,4α(IE,3R*),5β,6aα]]-hexahydro-5-[[(1,1-dimethylethyl)dimethylsilyl]oxy]-4-[[[3-(1,1-dimethylethyl)dimethylsilyl]oxy]-4,4-dimethyl-l-octenyl]-2H-cyclopenta[b]furan-2-one as a white amorphous solid was obtained; mp 67°–68°.

EXAMPLE 2

[3aR-[3aα,4α(1E,3R*),5β,6aα]]-4,5,6,6a-Tetrahydro-5-[[1,1-dimethylethyl)dimethylsilyl]-oxy]-4-[[[3-(1,1-dimethylethyl)dimethylsilyl]oxy]-4,4-dimethyl-l-octenyl]-2-(trimethylsilyl)oxy-3aH-cyclopenta[b]furan 570 μl (4.07 mmol) of diisopropylamine (dist. from $CaH_2$) was dissolved in 15 ml of tetrahydrofuran (freshyl dist. from LAH). The mixture was cooled to +3° C. under a positive argon pressure. 2.5 ml (3.75 mmol) of 1.5N n-butyllithium in hexane was added dropwise at +3° C. After stirring at +3° C. for 5 min, the mixture was cooled to −40° C. with a dry ice/acetone bath. 1.757 g (3.35 mmol) of [3aR-[3aα,4α(1E,3R*),5β,6aα]-]hexahydro-5-[[(1,1-dimethylethyl)dimethylsilyl]oxy]-4-[[[3-(1,1-dimethylethyl)dimethylsilyl]oxy]-4,4-dimethyl-l-octenyl]-2H-cyclopenta[b]furan-2-one dissolved in 6 ml THF was added dropwise to the lithium diisopropylamide solution at −40° C. After stirring at −40° C. for an additional 5 min, 570 μl (4.49 mmol) of trimethylchlorosilane (dist.) was added rapidly. Two min after the addition, the cooling bath was removed and the mixture was allowed to warm to +15° C. over a 20 min period. The solvent was removed under vacuum (ca 0.2 MMHG) at or below room temperature and the residue was dried at high vacuum for 15 min. 10 mL of ether (freshly filtered through aluminum oxide, activityl) was added under argon and the mixture was filtered through a sintered glass funnel. The white residue was washed three times with 3 mL of ether. The slightly yellow filtrate was concentrated under vacuum and the oily residue was dried at high vacuum (room temperature) for 1 h. producing [3aR-[3aα,4α(1E,3R*),5β,6aα]]-4,5,6,6a-tetrahydro-5-[[[1,1-dimethylethyl)dimethylsilyl]oxy-4-[[[3-(1,1-dimethylethyl)dimethylsilyl]-oxy]-4,4-dimethyl-1-octenyl]-2-(trimethylsilyl)oxy-3aH-cyclopenta[b]furan.

EXAMPLE 3

[3S-[3α,3aα,4α(1E,3R*),5β,6aα]]-Hexahydro-3-fluoro-5-[[(1,1-dimethylethyl)dimethylsilyl]-oxy]-4-[[[3-(1,1-dimethylethyl)dimethylsilyl]oxy]-4,4-dimethyl-1-ocetenyl]-2H-cyclopenta[b]furan-2-one The compound [3aR-[3aα,4α(1E,3R*),5β,6aα]]-4,5,6,6a-tetrahydro-5-[[1,1-dimethylethyl)dimethylsilyl]oxy-4-[[[3-(1,1-dimethylethyl)dimethylsilyl]oxy]-4,4-dimethyl-1-octenyl]-2-(trimethylsilyl)oxy-3aH-cyclopenta[b]furan was dissolved in 15 mL of methylene chloride (freshly filtered through aluminum oxide, activity I) under argon. The mixture was cooled to +2° C. with an ice/water bath. 680 mg (6.8 mmol) of potassium bicarbonate (dried at high vacuum at 100° over $P_2O_5$ for 3 h) followed by 632.9 mg (3.73 mmol) of xenon difluoride were added under stirring. An immediate reaction ensued as judged by the vigorous gas evolution in the first 30 sec. after the addition of $XeF_2$. The mixture was stirred at +2° C. for 20 min, poured into 150 mL of ice cold water and extracted three times with 150 ml of methylene chloride. The extracts were washed twice with 150 ml of brine, combined, dried over MgSO$_4$ and concentrated at reduced pressure. The residue was dried at high vacuum for 18 h leaving 1.92 g of a yellowish oil.

The crude product was chromatographed on 200 g of silica gel (230–400 mesh) using the flash chromatography technique. 5% by volume ethyl acetate/95% by volume petroleum ether (1 lt) followed by 10% ethyl acetate/petroleum ether were used as eluting solvents. The following products were obtained in order of elution: 1.06 g (1.95 mmol) 58% of [3S-[3α,3aα,4α(1E,3R*),5β,6aα]]-hexahydro-3-fluoro-5-[[(1,1-dimethylethyl)-dimethylsilyl]oxy]-4-[[[3-(1,1-dimethylethyl)dimethylsilyl]-oxy]-4,4-dimethyl-1-octenyl]-2H-cyclopenta[b]furan-2-one; white needles formed on standing, m.p. 49°–51°; 165.2 mg (0.315 mmol) 9.4% of [3aR-[3aα,4α-(1E,3R*),5β,6aα]]-hexahydro-5-[[(1,1-dimethylethyl)-dimethylsilyl]exyl]-4-[[[3-(1,1-dimethylethyl)dimethyl-silyl]oxy]-4,4-dimethyl-1-octenyl]-2H-cyclopenta[b]furan-2-one, starting material; and 98.9 mg (0.182 mmol) 5.4% of 3R-[3β,3aα,4α(1E,3R*),5β,6aα]-hexahydro-3-fluoro-5-[[(1,1-dimethylethyl)dimethylsilyl]oxy]-4-[[[3-(1,1-dimethylethyl)dimethylsilyl]-oxy]-4,4-dimethyl-1-octenyl]-2H-cyclopenta[b]furan-2-one; amorphous white solid; m.p. 83°–85°.

EXAMPLE 4

[3S-[3α,3aα,4α(1E,3R*),5β,6aα]]-Hexahydro-3-fluoro-5-hydroxy-4-(3-hydroxy-4,4-dimethyl-1-octenyl)-2H-cyclopenta[b]furan-2-one 1.597 g (2.94 mmol) of the fluoro lactone [3S-[3α,3aα,4α(1E,3R*),5β,6aα]]-hexahydro-3-fluoro-5-[[(1,1-dimethylethyl)dimethylsilyl]oxy]-4-[[[3-(1,1-dimethylethyl)dimethylsilyl]oxy]-4,4-dimethyl-1-octenyl]-2H-cyclopenta[b]furan-2-one was dissolved in 60 ml of acetic acid (reagent grade) and the mixture was warmed to 55° C. under a positive argon pressure. 6 ml of water was added with stirring at 55° C. After 7 h, an additional 4 ml of water was added and stirring at 55° C. was continued for 64 h (71 h total). After cooling to room temperature, the solvent was removed under vacuum (ca. 0.2 Torr) at 25°–30° C. The oily residue was dried at high vacuum for 2 h at room temperature, followed by chromatography on 200 g of silica gel (230–400 mesh) using solvent mixtures ranging from ethyl acetate/petroleum ether 1:1 parts by volume to pure ethyl acetate for elution.

351.2 mg of partially hydrolyzed material containing large amounts of impurities and 571.5 mg (1.82 mmole, 62%) of [3S-[3α,3aα,4α(1E,3R*),5β6aα]]-hexahydro-3-fluoro-5-hydroxy-4-(3-hydroxy-4,4-dimethyl-1-octenyl)-2H-cyclopenta[b]furan-2-one (oil) were obtained. Resubjecting the 351.2 mg of partially hydrolyzed material to similar reaction conditions (HOAc, H$_2$O) for 42 h resulted in the formation of 39.6 mg (0.126 mmole) 4.3% of additional [3S-[3α,3aα,4α(-1E,3R*),5β,6aα]]-hexahydro-3-fluoro-5-hydroxy-4-(3-hydroxy-4,4-dimethyl-1-octenyl)-2H-cyclopenta[b]furan-2-one. Total yield of [3S-[3α,3aα,4α(1E,3R*),5β,6aα]]-hexahydro-3-fluoro-5-hydroxy-4-(3-hydroxy-4,4-dimethyl-1-octenyl)-2H-cyclopenta[b]furan-2-one was 611.1 mg (1.94 mmol) 66%, oil, clear.

EXAMPLE 5

[3S-[3α,3aα,4α(1E,3R*),5β,6aα]]-Hexahydro-3-fluoro-5-[(tetrahydro-2H-pyran-2-yl)oxy]-4-[3-(tetrahydro-2H-pyran-2-yl)oxy]-4,4-dimethyl-1-octenyl]-2H-cyclopenta[b]furan-2-one 571.5 mg (1.82 mmol) of [3S-[3α,3aα,4α(1E,3R*),5β,6aα]]-hexahydro-3-fluoro-5-hydroxy-4-(3-hydroxy-4,4-dimethyl-1-octenyl)-2H-cyclopenta[b]furan-2-one was dissolved in 20 ml of methylene chloride (freshly filtered through aluminum oxide, activity I) under a positive argon pressure. 2.0 ml (21.9 mmol) of dihydropyran (freshly dist. from sodium) was added under stirring followed by a crystal of p-toluenesulfonic acid monohydrate (9.7 mg; 0.05 mmol). The mixture was stirred at room temperature for 30 min, poured into 50 ml of sat. aqueous sodium bicarbonate and extracted three times with 30 ml of methylene chloride. The extracts were washed twice with 50 ml of brine, combined, dried over MgSO$_4$ and concentrated at reduced pressure. The crude product (1.14 g, oil) was chromatographed on a 100 g silica gel column with ether/petroleum ether (1:1) yielding 797 mg (1.65 mmol) 91% of [3S-[3α,3aα,4α(1E,3R*),5β,6aα]]-hexahydro-3-fluoro-5-[(tetrahydro-2H-pyran-2-yl)oxy]-4-[3-(tetrahydro-2H-pyran-2-yl)oxy]-4,4-dimethyl-1-octenyl]-2H-cyclopenta[b]furan-2-one as a clear oil (mixture of THP-diastereomers). $[\alpha]_D^{25}$ −32.46° in CHCl$_3$, c=0.8780.

EXAMPLE 6

[3S-[3α,3aα,4α(1E,3R*),5β,6aα]]-Hexahydro-3-fluoro-5[(tetrahydro-2H-pyran-2-yl)oxy]-4-[3-(tetrahydro-2H-pyran-2-yl)oxy]-4,4-dimethyl-1-octenyl]-2H-cyclopenta[b]furan-2-ol After dissolving 729.2 mg (1.51 mmol) of [3S-[3α,3aα,4α(1E,3R*),5β,6aα]]-hexahydro-3-fluoro-5-[(tetrahydro-2H-pyran-2-yl)oxy]-4-[3-[(tetrahydro-2H-pyran-2-yl)oxy]-4,4-dimethyl-1-octenyl]-2H-cyclopenta[b]furan-2-one in 10 ml of toluene (dist. from CaH$_2$) under argon, the mixture was cooled to approx. −70° C. with a dry ice/acetone bath. 1.25 ml (1.75 mmol) of a 1.4M solution of diisobutylaluminum hydride in hexane was added dropwise at −70° C. The mixture was stirred at −70° C. for 20 min. 3 ml of a saturated aqueous ammonium chloride solution was added dropwise at −70° C. and the resulting mixture was transferred with 20 ml of water and 50 ml of ethyl acetate into a separatory funnel. Shaking caused a very thick suspension to form, which was filtered through celite. The residue was washed thoroughly with 100 ml of ethyl acetate. The filtrate was again transferred into a separatory funnel and washed once with 60 ml of brine/water (1:1 parts by volume) and once with 100 ml brine. The aqueous washings were reextracted once with 80 ml of ethyl acetate. The organic extracts were combined, dried over MgSO$_4$ and concentrated at reduced pressure. Flash chromatography on 200 g of silica gel (230–400 mesh) of the crude product (806 mg; oil) with ethyl acetate/petroleum ether (4:6) gave 661.5 mg (1.36 mmol) 90% of [3S-[3α,3aα,4α(1E,3R*),5β,6aα]]-hexahydro-3-fluoro-5[(tetrahydro-2H-pyran-2-yl)oxy]-4-[3-[(tetrahydro-2H-pyran-2-yl)oxy]-4,4-dimethyl-1-octenyl]-2H-cyclopenta[b]furan-2-ol as an amorphous solid, m.p. 58°–66° C.; $[\alpha]_D^{25}$=−12.83° in CHCl$_3$, c=1.0290.

EXAMPLE 7

(5Z,7R,9α,11α,13E,15R)-7-Fluoro-11,15-di[(tetrahydro-2H-pyran-2-yl)oxy]-16,16-dimethyl-9-hydroxy-prosta-5,13-dien-1-oic acid methyl ester 1.54 g (3.47 mmol) of (4-carboxybutyl)triphenylphosphonium bromide (dried at high vacuum at 100° over $P_2O_5$ for 2 h) and 1.275 g (6.95 mmol) of sodium hexamethyldisilazane (dist.) were placed into a three neck flask under argon. 20 ml of tetrahydrofuran (freshly dist. from LAH) and 1.25 mL (7.18 mmol) of hexamethylphosphoramide (dist.) were added. This mixture was stirred at room temperature for 1½ h. To the orange red suspension was added dropwise a solution of 560.5 mg (1.16 mmol) of [3S-[3α,3aα,4α(1E,3R*),5β,6aα]-hexahydro-3-fluoro-5[(tetrahydro-2H-pyran-2-yl)oxy]-4-[3-[(tetrahydro-2H-pyran-2-yl)oxy]-4,4-dimethyl-1-octenyl]-2H-cyclopenta[b]furan-2-ol in 4 ml of tetrahydrofuran. The resulting yellow-orange mixture was stirred at room temperature for 4 h. The reaction was quenched by the dropwise addition of glacial acedic acid (faint yellow color). Most of the solvent was evaporated under high vacuum at or below room temperature. The residue was transferred with 100 mL of ether and 100 ml of water into a separatory funnel. The aqueous phase was acidified to pH 3 with 13 mL of 1N HCl. After shaking and separation of the two phases, the aqueous phase was reextracted twice with 70 mL of ether. The organic extracts were washed twice with 70 ml of brine, combined and dried over $MgSO_4$. After removal of the solvent, the oily residue was dried at high vacuum for 1½ h, leaving 1.45 g of an oil. This crude acid was dissolved in 10 mL of methylene chloride (freshly filtered through aluminum oxide, activity I) and esterified at room temperature by the addition of 15 mL (3.75 mmol) of a 0.25N solution of diazomethane in ether. After removal of the solvent at aspirator pressure, the remaining oil (1.27 g) was dissolved in 10 mL of tetrahydrofuran and 2.8 mL (2.8 mmol) of a 1.0M solution of tetra-n-butylammonium fluoride in tetrahydrofuran was added. The mixture was stirred at room temperature for 15 min, poured into 100 ml of a half concentrated aqueous ammonium chloride solution and extracted three times with 100 ml of ether. The extracts were washed twice with 70 ml of brine, combined, dried over $MgSO_4$ and concentrated at reduced pressure. 1.24 g of a yellow oil was obtained. Chromatography on 100 g of silica gel with ethyl acetate/petroleum ether (3:7) (700 ml) followed by ethyl acetate/petroleum ether (1:1 parts by volume) gave 20.8 mg (3.7%) of [3S-[3α,3aα,4α(1E,3R*),5β,6aα]]-hexahydro-3-fluoro-5[(tetrahydro-2H-pyran-2-yl)oxy]-4-[3-[(tetrahydro-2H-pyran-2-yl)oxy]-4,4-dimethyl-1-octenyl]-2H-cyclopenta[b]furan-2-ol (starting material) and 496.3 mg (0.85 mmol) 73% of (5Z,7R,9α,11α,13E,15R)-7-fluoro-11,15-di[(tetrahydro-2H-pyran-2-yl)oxy]-16,16-dimethyl-9-hydroxy-prosta-5,13-dien-1-oic acid methylester (oil), as a mixture of diastereomers; $[α]_D^{25} = +2.74°$ in $CHCl_3$, c=0.9116.

EXAMPLE 8

(7β,9α,11α,13E,15R)-16,16-Dimethyl-11,15-di[(tetrahydro-2H-pyran-2-yl)oxy]-6,9-epoxy-7-fluoro-5-iodo-prosta-13-en-1-oic acid methyl ester 246.9 mg (0.424 mmol) of (5Z,7R,9α,11α,13E,15R)-7-fluoro-11,15-di[(tetrahydro-2H-pyran-2-yl)oxy]-16,16-dimethyl-9-hydroxy-prosta-5,13-dien-1-oic acid methyl ester was dissolved in 10 mL of acetonitrile (dried over 3A molecular sieves) under a positive argon pressure. 476.9 mg (2.12 mmol, 5 eq.) of N-iodo succinimide was added under stirring, the flask was flushed with argon, closed with a stopper and wrapped in aluminum foil to protect the reaction mixture from light. The mixture was stirred at room temperature for 27 h, poured into 100 mL of a 10% weight by volume solution of sodium thiosulfate in water and extracted three times with 100 mL of methylene chloride. The organic extracts were washed twice with 100 ml of brine, combined, dried over $MgSO_4$ and concentrated at aspirator pressure. 285.9 mg of an oily residue was obtained. Chromatography on 75 g of silica gel with ether/petroleum ether (1:1 parts by volume) gave 186.7 mg (0.263 mmol) 62% of (7β,9α,11α,13E,15R)-16,16-dimethyl-11,15-di[(tetrahydro-2H-pyran-2-yl)oxy]-6,9-epoxy-7-fluoro-5-iodo-prosta-13-cn-1-oic acid methyl ester (oil) as a mixture of diastereomers.

EXAMPLE 9

(7β,9α,11α,13E,15R)-16,16-Dimethyl-11,15-dihydroxy-6,9-epoxy-7-fluoro-5-iodo-prosta-13-en-1-oic acid methyl ester 10.6 mg (15 μmol) of (7β,9α,11α,13E,15R)-16,16-dimethyl-11,15-di[(tetrahydro-2H-pyran-2-yl)oxy]-6,9-epoxy-7-fluoro-5-iodo-prosta-13-en-1-oic acid methyl ester was dissolved in a mixture of 3 mL of tetrahydrofuran (freshly dist. from LAH), 6 mL of glacial acetic acid and 3 mL of water under a positive argon pressure. The mixture was heated in an oil bath at 40° C. and stirred for 19 h. After cooling to room temperature, the solvent was removed at high vacuum at 25°. 2 mL of toluene was added and the solvent was again removed at high vacuum at 25°. The oily residue (11.2 mg) was chromatographed on a thin layer silica gel plate with ether giving 6.3 mg (11.65 mol, 78%) of (7β,9α,11α,13E,15R)-16,16-dimethyl-11,15-dihydroxy-6,9-epoxy-7-fluoro-5-iodo-prosta-13-en-1-oic acid methyl ester (oil) as a mixture of isomers.

EXAMPLE 10

(5Z,7β,9α,11α,13E,15R)-7-fluoro-6,9-epoxy-11,15-dihydroxy-16,16-dimethyl-prosta-5,13-dien-1-oic acid methyl ester 6.3 mg (11.66 μmol) of (7β,9α,11α,13E,15R)-16,16-dimethyl-11,15-dihydroxy-6,9-epoxy-7-fluoro-5-iodo-prosta-13-en-1-oic acid methyl ester (mixture of isomers) was dissolved in 2.0 mL of toluene (dist. from $CaH_2$) under a positive argon pressure. 20 μl (134 μmol) of 1,8-diazabicyclo[54.0]undec-7-ene (dist. from $CaH_2$) was added. With stirring, the mixture was slowly heated to 90° C. (over 90 min) and kept at 90° C. for 22 h. After cooling to room temperature, the mixture was poured into 75 ml of half saturated brine and extracted three times with 20 mL of ether. The extracts were washed once with 20 mL of brine, combined, dried over $MgSO_4$ and concentrated at aspirator pressure. The remaining oil was dried at high vacuum for 3 h and the 6.2 mg of residual oil was chromatographed on a thin layer silica gel plate with ethyl acetate. Two products were isolated: 3.0 mg (7.27 μmol) 62% of (5Z,7β,9α,11α,13E,15R)-7-fluoro-6,9-epoxy-11,15-dihydroxy-16,16-dimethyl-prosta-5,13-dien-1-oic acid methyl ester (oil) and 1.1 mg (2.66 μmol) 23% of (4E,6α,7β,9α,11α,13E,15R)-7-fluoro-6,9-epoxy-11,15-dihydroxy- 16,16-dimethyl-prosta-4,13-dien-1-oic acid methyl ester (oil).

EXAMPLE 11

(5Z,7β,9α,11α,13E,15R)-7-Fluoro-6,9-epoxy-11,15-dihydroxy-16,16-dimethyl-prosta-5,13-dien-1-oic acid sodium salt 3.0 mg (7.27 82 mole) of (5Z,7β,9α,11α,13E,15R)-7-fluoro-6,9-epoxy-11,15-dihydroxy-16,16-dimethyl-prosta-5,13-dien-1-oic acid methyl ester was dissolved in 0.5 ml methanol and 0.5 ml water under argon. 73 μl (7.3 μmole = 1 eq) 0.1N sodium hydroxide was added and the mixture was stirred at room temperature for 2 hr. The methanol was removed at reduced pressure and the remaining aqueous solution was lyophilized to give (5Z,7β,9α,11α,13E,15R)-7-fluoro-6,9-epoxy-11,15-dihydroxy-16,16-dimethyl-prosta-5,13-dien-1-oic acid sodium salt as a white powder; m.p. 48°-51° C.

EXAMPLE 12

[3aR-[3aα,4α(1E,3R*,4R*)6aα]]-Hexahydro-4-[[[3-(1,1-dimethylethyl)dimethylsilyl]oxy]-4-fluoro-1-octenyl]-2H-cyclopenta[b]furan-2-one By the procedure of Example 1 [3aR-3aα,4α(1E,3R*,4R*)6aα]]-Hexahydro-4-[4-fluoro-3-hydroxy-1-octenyl)-2H-cyclopenta[b]furan-2-one was converted to [3aR-[3aα,4α(1E,3R*,4R*)6aα]]-hexahydro-4-[[[3-(1,1-dimethylethyl)dimethylsilyl]oxy]-4-fluoro-1-octenyl]-2H-cyclopenta[b]furan-2-one.

EXAMPLE 13

[3aR-[3aα,4α(1E,3R*,4R*)6aα]]-Hexahydro-3-fluoro-4-[[[3-(1,1-dimethylethyl)dimethylsilyl]oxy]-4-fluoro-1-octenyl]-2H-cyclopenta[b]furan-2-one By the procedure of Examples 2 and 3, [3aR-[3aα,4α(1E,3R*,4R*)6aα]]-hexahydro-4-[[[3-(1,1-dimethylethyl)dimethylsilyl]oxy]-4-fluoro-1-octenyl]-2H-cyclopenta[b]furan-2-one was converted to [3aR-[3aα,4α(1E,3R*,4R*)6aα]]-hexahydro-3-fluoro-4-[[[3-(1,1-dimethylethyl)dimethylsilyl]oxy]-4-fluoro-1-octenyl]-2H-furan-2-one.

EXAMPLE 14

[3aR-[3aα,4α(1E,3R*,4R*)6aα]]-Hexahydro-3-fluoro-4-(3-hydroxy-4-fluoro-1-octenyl]-2H-cyclopenta[b]furan-2-one By the procedure of Example 4 [3aR-[3aα,4α(1E,3R*,4R*)6aα]]-hexahydro-3-fluoro-4-[[[3-(1,1-dimethylethyl)dimethylsilyl]oxy]-4-fluoro-1-octenyl]-2H-cyclopenta[b]furan-2-one was converted to [3aR-[3aα,4α(1E,3R*,4R*)6aα]]-hexahydro-3-fluoro-4-(3-hydroxy-4-fluoro-1-octenyl]-2H-cyclopenta[b]furan-2-one.

EXAMPLE 15

[3aR-[3aα,4α(1E,3R*,4R*)6aα]]-Hexahydro-3-fluoro-4-[3-[(tetrahydro-2H-pyran-2-yl)oxy]-4-fluoro-1-octenyl]-2H-cyclopenta[b]furan-2-one By the procedure of Example 5 [3aR-[3aα,4α(1E,3R*,4R*)6aα]]-hexahydro-3-fluoro-4-(3-hydroxy-4-fluoro-1-octenyl)-2H-cyclopenta[b]furan-2-one was converted to [3aR-[3aα,4α(1E,3R*,4R*)6aα]]-hexahydro-3-fluoro-4-[3-[(tetrahydro-2H-pyran-2-yl)oxy]-4-fluoro-1-octenyl]-2H-cyclopenta[b]furan-2-one.

EXAMPLE 16

[3aR-[3aα,4α(1E,3R*,4R*)6aα]]-Hexahydro-3-fluoro-4-[3-[(tetrahydro-2H-pyran-2-yl)oxy]-4-fluoro-1-octenyl]-2H-cyclopenta[b]furan-2-ol By the procedure of Example 6 [3aR-[3aα,4α(1E,3R*,4R*)6aα]]-hexahydro-3-fluoro-4-[3-[(tetrahydro-2H-pyran-2-yl)oxy]-4-fluoro-1-octenyl]-2H-cyclopenta[b]furan-2-one was converted to [3aR-[3aα,4α(1E,3R*,4R*)6aα]]-hexahydro-3-fluoro-4-[3-[(tetrahydro-pyran-2-yl)oxy]-4-fluoro-1-octenyl]-2H-cyclopenta[b]furan-2-ol.

EXAMPLE 17

(5Z,9α,13E,15R,16R)-7,16-Difluoro-15[(tetrahydro-2H-pyran-2-yl)oxy]-9-hydroxy-5,13-dien-1-oic acid methyl ester By the procedure of Example 7 [3aR-[3aα,4α(1E,3R*,4R*)6aα]]-hexahydro-3-fluoro-4[3-[(tetrahydro-2H-pyran-2-yl)oxy]-4-fluoro-1-octenyl]-2H-cyclopenta[b]furan-2-ol was converted to (5Z,9α,13E,15R,16R)-7,16-difluoro-15[(tetrahydro-2H-pyran-2-yl)oxy]-9-hydroxy-prosta-5,13-dien-1-oic acid methyl ester.

EXAMPLE 18

(9α,13E,15R,16R)-7,16-Difluoro-15[(tetrahydro-2H-pyran-2-yl)oxy]-6,9-epoxy-5-iodo-prosta-13-en-1-oic acid methyl ester By the procedure of Example 8, (5Z,9α,13E,15R,16R)-7,16-difluoro-15[(tetrahydro-2H-pyran-2-yl)oxy]-9-hydroxy-prosta-5,13-dien-1-oic acid methyl ester was converted to (9α,13E,15R,16R)-7,16-difluoro-15[(tetrahydro-2H-pyran-2-yl)oxy]-6,9-epoxy-5-iodo-prosta-13-en-1-oic acid methyl ester.

EXAMPLE 19

(9α,13E,15R,16R)-7,16-Difluoro-15-hydroxy-6,9-epoxy-5-iodo-prosta-13-en-1-oic acid methyl ester By the procedure of Example 9, (9α,13E,15R,16R)-7,16-difluoro-15[(tetrahydro-2H-pyran-2-yl)oxy]-6,9-epoxy-5-iodo-prosta-13-en-1-oic acid methyl ester was converted to (9α,13E,15R,16R)-7,16-difluoro-15-hydroxy-6,9-epoxy-5-iodo-prosta-13-en-1-oic acid methyl ester.

EXAMPLE 20

(5Z,9α,13E,15R,16R)-7,16-Difluoro-6,9-epoxy-15-hydroxy-prosta-5,13-dien-1-oic acid methyl ester By the procedure of Example 10 (9α,13E,15R,16R)-7,16-difluoro-15-hydroxy-6,9-epoxy-5-iodo-prosta-13-en-1-oic acid methyl ester was converted to (5Z,9α,13E,15R,16R)-7,16-difluoro-15-hydroxy-6,9-epoxy-prosta-5,13-dien-1-oic acid methyl ester.

EXAMPLE 21

(5Z,9α,13E,15R,16R)-7,16-Difluoro-6,9-epoxy-15-hydroxy-prosta-5,13-dien-1-oic acid sodium salt By the procedure of Example 11, (5Z,9α,13E,15R,16R)-7,16-difluoro-6,9-epoxy-15-hydroxy-prosta-5,13-dien-1-oic acid methyl ester was converted to (5Z,9α,13E,15R,16R)-7,16-difluoro-6,9-epoxy-15-hydroxy-prosta-5,13-dien-1-oic acid sodium salt.

EXAMPLE 22

(4E,9α,13E,15R,16R)-7,16-Difluoro-6,19-epoxy-15-hydroxy-prosta-4,13-dien-1-oic acid methyl ester By the procedure of Example 10, (9α,13E,15R,16R)-7,16-difluoro-15-hydroxy-6,9-epoxy-5-iodo-prosta-13-en-1-oic acid methyl ester was converted to (4E,9α,13E,15R,16R)-7,16-difluoro-6,9-epoxy-15-hydroxy-prosta-4,13-dien-1-oic acid methyl ester.

EXAMPLE 23

By the procedure of Example 11, (4E,9α,13E,15R,16R)-7,16-difluoro-6,9-epoxy-15-hydroxy-prosta-4,13-dien-1-oic acid methyl ester was converted to the sodium salt of (4E,9α,13E,15R,16R)-7,16-difluoro-6,9-epoxy-15-hydroxy-prosta-4,13-dien-1-oic acid.

EXAMPLE 24

A tablet was found containing:

|  | Per Tablet |
|---|---|
| (5Z,9α,13E,15R,16R)-7,16-Difluoro-6,9-epoxy-15-hydroxy-prosta-5,13-dien-1-oic acid sodium salt | 25 mg. |
| Dicalcium phosphate dihydrate, unmilled | 175 mg. |
| Corn Starch | 24 mg. |
| Magnesium stearate | 1 mg. |
| Total Weight | 225 mg. |

The active ingredient and corn starch were mixed together and passed through a #00 screen in Model "J" Fitzmill with hammers forward. This premix was then mixed with dicalcium phosphate and one-half of the magnesium stearate, passed through a #1Z screen in Model "J" Fitzmill with kniver forward, and slugged. The slugs were passed through a #2A plate in a Model "D" Fitzmill at slow speed with knives forward and the remaining magnesium stearate was added. The mixture was mixed and compressed.

EXAMPLE 25

A tablet was formulated in the same manner as in Example 24 except that (4E,9α,13E,15R,16R)-7,16-difluoro-6,9-epoxy-15-hydroxy-prosta-4,13-dien-1-oic acid methyl ester was the active ingredient.

EXAMPLE 26

A capsule was prepared containing the following ingredients:

|  | Per Tablet |
|---|---|
| (5Z,9α,13E,15R,16R)-7,16-difluoro-6,9-epoxy-15-hydroxy-prosta-5,13-dien-1-oic acid sodium salt | 200 mg. |
| Dicalcium phosphate dihydrate, unmilled | 235 mg. |
| Corn Starch | 70 mg. |
| FD & C Yellow #5 - Aluminum Lake 25% | 2 mg. |
| Durkee Duratex* | 25 mg. |
| Calcium Stearate | 3 mg. |
|  | 535 mg. |

*Hydrogenated cotton seed oil (fully saturated)

All of the above ingredients were mixed until thoroughly blended in a suitable size container. The powder was filled in to #2, two-piece, hard-shell gelatin capsules to an approximately fill weight of 350 mg using a capsulating machine.

EXAMPLE 27

A capsule was prepared by the procedure of example 24 except that (4E,9α,13E,15R,16R)-7,16-difluoro-6,9-epoxy-15-hydroxy-prosta-4,13-dien-1-oic acid methyl ester was the active ingredient.

EXAMPLE 28

3,3aS,4,5,6,6aS-Hexahydro-3-fluoro-4R-[4,4-dimethyl-3R-(2-tetrahydropyranyloxy)-1-trans-octenyl]-5R-methyl-2H-cyclopenta[b]furan-2-one To a solution of diisopropylamine in 9 ml of THF (tetrahydrofuran) cooled to 0°–5° C., was added dropwise 1.32 ml of a 2.2M solution of n-butyl lithium in hexane. The mixture was stirred for 5 min. and cooled to −40° C. with a dry ice acetone bath. A solution of 1 g of 3,3aR,4,5,6,6aS-hexahydro-4R[4,4-dimethyl-3R-(2-tetrahydropyranyloxy)-1-trans-octenyl]-5R-methyl-2H-cyclopenta[b]furan-2-one in 6 ml of THF (tetrahydrofuran) was added dropwise over 1 minute and stirred at −45° C. for 5 min. Trimethylchlorosilane (4.26 ml) was then added and the mixture stirred at −40° C. for 5 min. The mixture was then allowed to warm to 0° C. and the solvent removed under high vacuum. Diethyl ether (5 ml) was added to the residue and the cold mixture filtered through a sintered glass funnel. The solvent was then removed under high vacuum (ice bath) and the residue dissolved in 10 ml of $CH_2Cl_2$. To the solution at 0° C. was then added 530 mg of potassium bicarbonate followed by 429 mg of xenon difluoride. After the gas evolution ceased, the mixture was stirred for an additional 15 min. and diluted with 50 ml of $CH_2Cl_2$. The solution was then washed with 50 ml of $H_2O + 2 \times 50$ ml of brine. The aqueous phase was separated and back washed with 50 ml of $CH_2Cl_2$. The organic layers were combined, dried ($MgSO_4$) and the solvents removed under reduced pressure to give 0.95 g of crude product. Chromatography on 50 g of silica gel afforded 300 mg of 3,3aS,4,5,6,6aS-hexahydro-3-fluoro-4R-[4,4-dimethyl-3R-(2-tetrahydropyranyloxy)-1-trans-octenyl]-5R-methyl-2H-cyclopenta[b]furan.

EXAMPLE 29

3,3aS,4,5,6,6aS-Hexahydro-3-fluoro-4R-[4,4-dimethyl-3R-(2-tetrahydropyranyloxy)-1-trans-octenyl]-5R-methyl-2H-cyclopenta[b]furan-2-ol By the procedure of Example 6,3,3aS,4,5,6,6aS-hexahydro-3-fluoro-4R-[4,4-dimethyl-3R-(2-tetrahydropyranyloxy)-1-trans-octenyl]-5R-methyl-2H-cyclopenta[b]furan-2-one was converted to 3,3aS,4,5,6,6aS-hexahydro-3-fluoro-4R[4,4-dimethyl-3R-(2-tetrahydropyranyloxy[-1-trans-octenyl]-5R-methyl-2H-cyclopenta[b]furan-2-ol.

EXAMPLE 30

11R,16,16-Trimethyl-7-fluoro-15R-(2-tetrahydropyranyloxy)-9S-hydroxyprosta-cis-5-trans-13-dienoic acid methyl ester By the procedure of Example 7,3,3aS,4,5,6,6aS-hexahydro-3-fluoro-4R[4,4-dimethyl-3R-(2-tetrahydropyranyloxy)-1-trans-octenyl]-5R-methyl-2H-cyclopenta[b]furan-2-ol was converted to 11R,16,16-trimethyl-7-fluoro-15R-(2-tetrahydropyranyloxy)-9S-hydroxyprosta-cis-5-trans-13-dienoic acid methyl ester.

EXAMPLE 31

(9S,11R,13E,15R)-11,16,16-Trimethyl-15-(2-tetrahydropyranyloxy)-6,9-epoxy-7-fluoro-5-iodoprosta-13-en-1-oic acid methyl ester By the procedure of Example 8, 11R,16,16-trimethyl-7-fluoro-15R-(2-tetrahydropyranyloxy)-9S-hydroxy-prosta-cis-5-trans-13-dienoic acid methyl ester was converted to (9S,11R,13E,15R)-11,16,16-trimethyl-15(2-tetrahydropyranyloxy)-6,9-epoxy-7-fluoro-5-iodo-prosta-13-en-1-oic acid methyl ester.

EXAMPLE 32

(9S,11R,13E,15R)-11,16,16-Trimethyl-15-hydroxy-6,9-epoxy-7-fluoro-5-iodo-prosta-13-en-1-oic acid methyl ester By the procedure of Example 9, (9S,11R,13E,15R)-11,16,16-trimethyl-15-(2-tetrahydropyranyloxy)-6,9-epoxy-7-fluoro-5-iodo-prosta-13-en-1-oic acid methyl ester was converted to (9S,11R,13E,15R)-11,16,16-trimethyl-15-hydroxy-6,9-epoxy-7-fluoro-5-iodo-prosto-13-en-1-oic acid methyl ester.

EXAMPLE 33

(5Z,9S,11R,13E,15R)-11,16,16-Trimethyl-15-hydroxy-6,9-epoxy-7-fluoro-prosta-5,13-dien-1-oic acid methyl ester and
(4E,9S,11R,15R)-11,16,16-trimethyl-15-hydroxy-6,9-epoxy-7-fluoro-4,13-dien-1-oic acid methyl ester By the procedure of Example 10, (9S,11R,13E,15R)-11,16,16-trimethyl-15-hydroxy-6,9-epoxy-7-fluoro-5-iodo-prosta-13-en-1-oic acid methyl ester was converted to a mixture which was separated by the procedure of Example 10 to (5Z,9S,11R,13E,15R)-11,16,16-trimethyl-15-hydroxy-6,9-epoxy-7-fluoro-prosta-5,13-dien-1-oic acid methyl ester.

Calc. for $C_{24}H_{39}FO_4$: C, 70.21; H, 9.57; F, 4.63. Found: C, 70.00; H, 9.44; F, 4.49.

ir 3615,1733,1694 cm$^{-1}$; ultraviolet λ max 213 nm (ε=12000) and (4E,9S,11R,15R)-11,16,-16-trimethyl-15-hydroxy-6,9-epoxy-7-fluoro-4,13-dien-1-oic acid methyl ester, Calc.: C, 70.21; H, 9.57; F, 4.63. Found: C, 70.19; H, 9.52; F, 4.85.

ir 3615,1735,1670 cm$^{-1}$.

EXAMPLE 34

(5Z,9S,11R,13E,15R)-11,16,16-Trimethyl-15-hydroxy-6,9-epoxy-7-fluoro-prosta-5,13-dien-1-oic acid sodium salt By the procedure of Example 11, (5Z,9S,11R,13E,15R)-11,16,16-trimethyl-15-hydroxy-6,9-epoxy-7-fluoro-prosta-5,13-dien-1-oic acid methyl ester was converted to (5Z,9S,11R,13E,15R)-11,16,16-trimethyl-15-hydroxy-6,9-epoxy-7-fluoro-prosta-5,13-dien-1-oic acid sodium salt.

EXAMPLE 35

3,3aS,4,5,6,6aS-Hexahydro-3-fluoro-4R-[3S-(2-tetrahydropyranyloxy)-1-trans-octenyl]-5R-(2-tetrahydropyranyloxy)-2H-cyclopenta[b]furan-2-one By the procedure of Example 28, 3,3aR,4,5,6,6,aS-hexahydro-4R-[3S-(2-tetrahydropyranyloxy)-1-trans-octenyl]-5R-(2-tetrahydropyranyloxy)-2H-cyclopenta[b]furan-2-one was converted to 3,3aS,4,5,6,6aS-hexahydro-3-fluoro-4R-[3S-(2-tetrahydropyranyloxy)-1-trans-octenyl]-5R-(2-tetrahydropyranyloxy)-2H-cyclopenta[b]furan-2-one.

EXAMPLE 36

3,3aS,4,5,6,6aS-Hexahydro-3-fluoro-4R-[3S-(2-tetrahydropyranyloxy)-1-trans-octenyl]-5R-(2-tetrahydropyranyloxy)-2H-cyclopenta[b]furan-2-one By the procedure of Example 6,3,3aS,4,5,6,6,aS-hexahydro-3-fluoro-4R[3S-(2-tetrahydropyranyloxy)-1-trans-octenyl]-5R-(2-tetrahydropyranyloxy)-2H-cyclopenta[b]furan-2-one was converted to 3,3aS,4,5,6-,6aS-hexahydro-3-fluoro-4R-[3S-(2-tetrahydropyranyloxy)-1-trans-octenyl]-5R-(2-tetrahydropyranyloxy)-2-H-cyclopenta[b]furan-2-ol.

EXAMPLE 37

11R,15S-Di(2-tetrahydropyranyloxy)-7-fluoro-9S-hydroxy-prosta-cis-5-trans-13-dienoic acid methyl ester By the procedure of Example 7, 3,3aS,4,5,6,6aS-hexahydro-3-fluoro-4R-[3S-(2-tetrahydropyranyloxy)-2H-cyclopenta[b]furan-2-ol was converted to 11R,15S-di(2-tetrahydropyranyloxy)-7-fluoro-9S-hydroxy-prosta-cis-5-trans-13-dienoic acid methyl ester.

EXAMPLE 38

(9S,11R,13E,15S)-11,15-Di(2-tetrahydropyranyloxy)-6,9-epoxy-7-fluoro-5-iodo-prosta-13-en-1-oic acid methyl ester By the procedure of Example 8, 11R,15R-di(2-tetrahydropyranyloxy)-7-fluoro-9S-hydroxy-prosta-cis-5-trans-----dienoic acid methyl ester was converted to (9S,11R,13E,15S)-11,15-di(2-tetrahydropyranyloxy)-6,9-epoxy-7-fluoro-5-iodo-prosta-13-en-1-oic acid methyl ester.

EXAMPLE 39

(9S,11R,13E,15S)-11,15-Dihydroxy-6,9-epoxy-7-fluoro-5-iodo-prosta-13-en-1-oic acid methyl ester By the procedure of Example 9, (9S,11R,13E,15S)-11,15-di(2-tetrahydropyranyloxy)-6,9-epoxy-7-fluoro-5-prosta-13-en-1-oic acid methyl ester was converted to (9S,11R,13E,15S)-11,15-dihydroxy-6,9-epoxy-7-fluoro-5-iodo-prosta-13-en-1-oic acid methyl ester.

EXAMPLE 40

(5Z,9S,11R,13E,15S)-11,15-Dihydroxy-69-epoxy-7-fluoro-prosta-5,13-dien-1-oic acid methyl ester and
(4E,9S,11R,15R)-11,15-Dihydroxy-6,9-epoxy-7-fluoro-4,13-dien-1-oic acid methyl ester By the procedure of Example 10 (9S,11R,13E,15S)-11,15-dihydroxy-6,9-epoxy-7-fluoro-5-iodo-prosta-13-en-1-oic acid methyl ester was converted to a mixture which was separated in accordance with the procedure of Example 10 to produce (5Z,9S,11R,13E,15S)-11,15-dihydroxy-6,9-epoxy-7-fluoro-prosta-5,13-dien-1-oic acid methyl ester and (4E,9S,11R,15S)-11,15-dihydroxy-6,9-epoxy-7-fluoro-4,13-dien-1-oic acid methyl ester.

EXAMPLE 41

(5Z,9S,11R,13E,15S)-11,15-Dihydroxy-6,9-epoxy-7-fluoro-prosta-5,13-dien-1-oic acid sodium salt By the procedure of Example 11, (5Z,9S,11R,13E,15S)-11,15-dihydroxy-6,9-epoxy-7-fluoro-prosta-5,13-dien-1-oic acid methyl ester was converted to (5Z,9S,11R,13E,15S)-11,15-dihydroxy-6,9-epoxy-7-fluoro-prosta-5,13-dien-1-oic acid sodium salt.

We claim:

1. A compound of the formula:

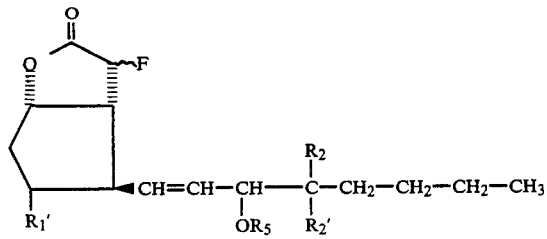

wherein $R_1'$ is hydrogen, methyl or —$OR_5$; $R_2$ is methyl, hydrogen or fluoro; $R_2'$ is fluoro, hydrogen, trifluoromethyl or methyl; —$OR_5$ is hydroxy or forms a hydrolyzable ether protecting group; and with the proviso that when $R_2'$ is trifluoromethyl, $R_2$ is hydrogen or methyl.

2. The compound of claim 1 wherein $R_1'$ is —$OR_5$.

3. The compound of claim 2 wherein said compound is [3S-[3α,3a,4a(IE,3R*),5β,6aα]]-hexahydro-3-fluoro-5-hydroxy-4-(3-hydroxy-4,4-dimethyl-1-octenyl)-2H-cyclopenta[b]furan-2-one.

4. The compound of claim 1 wherein said compound is [3aR[3aα,4α(1E,3R*,4R*)6aα]]-hexahydro-3-fluoro-4-(3-hydroxy-4-fluoro-1-octenyl)-2H-cyclopenta[b]furan-2-one.

* * * * *